(12) United States Patent
Li et al.

(10) Patent No.: US 8,242,073 B2
(45) Date of Patent: Aug. 14, 2012

(54) BIODEGRADABLE AND BIOABSORBABLE BIOMATERIALS AND KERATIN FIBROUS ARTICLES FOR MEDICAL APPLICATIONS

(75) Inventors: Yi Li, Kowloon (CN); Jiashen Li, Kowloon (CN); Junyan Hu, Kowloon (CN); Lin Li, Kowloon (CN)

(73) Assignee: The Hong Kong Polytechnic University, Hong Kong (CN)

( * ) Notice: Subject to any disclaimer, the term of this patent is extended or adjusted under 35 U.S.C. 154(b) by 893 days.

(21) Appl. No.: 12/216,717

(22) Filed: Jul. 10, 2008

(65) Prior Publication Data

US 2010/0009448 A1   Jan. 14, 2010

(51) Int. Cl.
*C07K 14/00* (2006.01)
*A61L 15/00* (2006.01)

(52) U.S. Cl. ............................................ 514/2; 424/445
(58) Field of Classification Search ........................ None
See application file for complete search history.

(56) References Cited

U.S. PATENT DOCUMENTS

| 6,306,424 | B1 | 10/2001 | Vyakanam et al. |
| 7,112,417 | B2 | 9/2006 | Vyakanam et al. |
| 7,674,882 | B2 * | 3/2010 | Kaplan et al. ............... 530/353 |
| 2007/0172651 | A1 * | 7/2007 | Miyoshi et al. ............ 428/373 |

OTHER PUBLICATIONS

Huang et al., "Engineered collagen-PEO nanofibers and fabrics", J. Biomater. Sci. Polymer Edn., vol. 12, No. 9, pp. 979-993 (2001).*

* cited by examiner

*Primary Examiner* — Anand Desai
(74) *Attorney, Agent, or Firm* — Wilkinson & Grist; George G. Wang

(57) ABSTRACT

The present invention relates to a process of making biodegradable and/or bioabsorbable biomaterials and keratin nonwoven fibrous articles by electrospinning fibers from a blend of biomaterials and keratin dissolved in organic solvents includes generating a high voltage electric field between oppositely charged biomaterials and keratin fluid in a syringe with a capillary tip and a metallic collection roller and causing a jet to flow to the roller as solvent evaporates and collecting fibrous membranes or scaffolds on the roller. Keratin increased the cell affinity of biomaterial scaffolds which have potential medical applications.

8 Claims, 6 Drawing Sheets

BIODEGRADABLE AND BIOABSORBABLE BIOMATERIALS AND KERATIN FIBROUS ARTICLES FOR MEDICAL APPLICATIONS

FIELD OF THE INVENTION

The present invention relates to methods for electrospinning fibrous biodegradable and/or bioabsorbable biomaterials and keratin membranes and scaffolds for medical applications.

BACKGROUND

The present invention is directed to products and methods having utility in medical applications. In one embodiment, the fibrous articles of the invention are polymeric membranes.

Electrospinning is a simple and low cost electrostatic self-assembly method capable of fabricating a large variety of fibers approximately 40 nm to 2 μm in diameter, in linear, 2-D and 3-D architecture. Electrospinning techniques have been available since the 1930's (U.S. Pat. No. 1,975,504). In the electrospinning process, there is a high voltage electric field between oppositely charged polymer fluid contained in a glass syringe with a capillary tip and a metallic collection target. As the voltage is increased to a critical value, the charge overcomes the surface tension of the suspended polymer cone formed on the capillary tip of the syringe of the glass pipette and a jet of ultrafine fibers is produced. As the charged fibers are sprayed, the solvent quickly evaporates and the fibers are accumulated randomly on the surface of the collection screen. This results in a nonwoven mesh of nano and micron scale fibers which has very large surface area to volume ratios and small pore sizes. Recently, electrospinning techniques have been developed and applied to the production of scaffolds in tissue engineering (Duan B, Yuan XY, et al. "A nanofibrous composite membrane of PLGA-chitosan/PVA was prepared by electrospinning", European Polymer Journal 2006; 42: 2013-2022).

In the present invention, electrospinning is used to produce fibrous composite from biomaterials and keratins for fabrication of membranes or scaffolds for medical applications. Examples of biodegradable and/or bioabsorbable biomaterials include, but are not limited to, poly(lactic acid), poly (glycolic acid), poly(lactic-co-glycolic acid). Food and Drug Administration (FDA) have approved these polymers for some human clinical applications, such as surgical sutures and implantable devices. One of their potential advantages is that their degradation rate can be adjusted to match the rate of regeneration of the new tissue. They can keep the framework until the new tissue forms because of their sufficient mechanical strength. They can also be fabricated to be the same complicated shapes or structures as the tissues or organs to be replaced. However, these are still some disadvantages, such as hydrophobicity, the lack of cell-recognition signals. These results that no sufficient cell attach on the surface of these polymer materials. The interaction between the host environment and these biomaterials still has much potential for improvement. Keratins are the major structure fibrous proteins constructing hair, wool, nail and so on, which are characteristically abundant in cysteine residues (7-20 number % of the total amino acid residues). As alternative natural proteinous biomaterials for collagen, wool keratins have been demonstrated to be useful for fibroblasts and osteoblasts, owing to their cell adhesion sequences, arginine-glycine-aspartic acid (RGD) and leucine-aspartic acid-vlaine (LDV), biocompatibility for modification targets. Moreover, they are biodegradable in vitro (by trypsin) and in vivo (by subcutaneous embedding in mice). Keratin sponges with controlled pore size and porosity was fabricated by a compression-modeling/particulate-leaching method.

The fibrous composite of biopolymers and keratins could combine their advantages together and have potential medical applications.

It is an object of the present invention to overcome the disadvantages and problems in the prior art.

SUMMARY OF THE INVENTION

The present invention uses electrospinning to prepare fibrous membranes and scaffolds of biodegradable and/or bioabsorbable biomaterials and keratin.

DESCRIPTION

Figure 1:
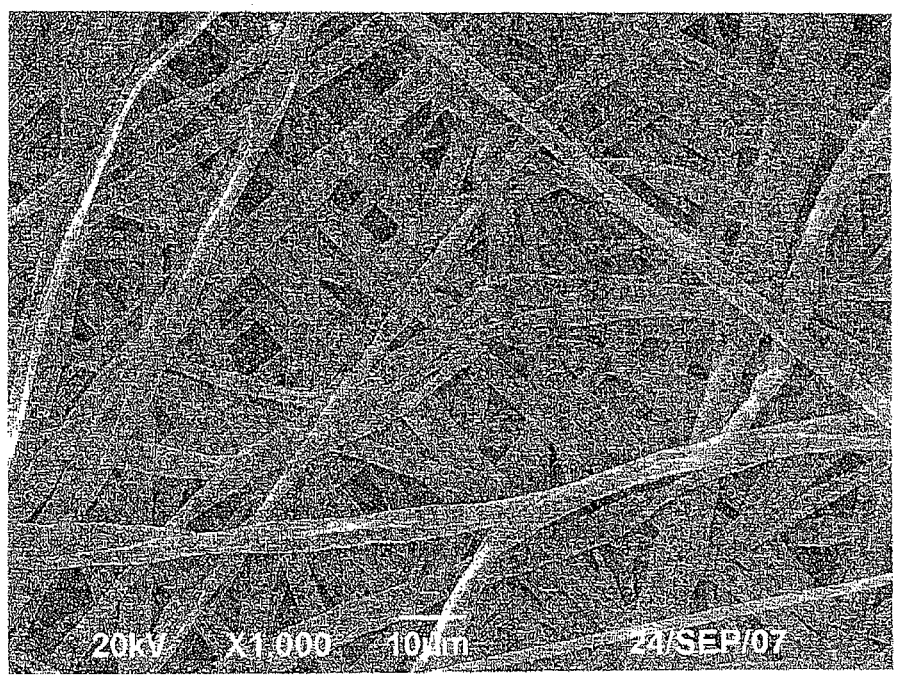
FIG. 1 is an SEM micrograph of PLLA electrospun membrane.

The present invention is directed to biodegradable and/or bioabsorable materials and keratin fibrous articles and cell culturing on these articles for medical applications. In one aspect, the invention relates to biodegradable and bioabsorbable fibrous articles formed by electrospinning of biodegradable and/or bioabsorbable materials. In another aspect, the articles contain composites of different biodegradable and/or bioabsorbable fibers. In yet another aspect, the articles can also include fibers of at least one biodegradable and/or bioabsorbable material which contains keratin.

A biodegradable material is intended to be broken down (usually gradually) by the body of an animal, e.g. a mammal. A bioabsorable material is intended to be absorbed or resorbed by the body of an animal, such that it eventually becomes essentially non-detectable at the site of application.

By the terminology "biodegradable and/or bioabsorable material" means that the material which is biocompatible, as well as biodegradable and/or bioabsorbable, and capable of being formed into fibers. The material can be formed into a fibrous article which is suitable for medical application and capable of being biodegraded and/bioabsorbed by the animal.

In a preferred embodiment, the biodegradable and/or bioabsorbable polymer was produced from a monomer selected from the group consisting of a glycolide, lactide, dioxanone, caprolactone, trimethylene carbonate, ethylene glycol, and lysine. The polymer can be a homopolymer, random or block co-polymer or hetero-polymer containing any combination of these monomers. The material can be a random copolymer, block copolymer or blend of homopolymers, copolymers, and/or heteropolymers that contain these monomers.

In one embodiment, the biodegradable and/or bioabsorbable polymer contains bioabsorbable and biodegradable linear aliphatic polyesters such as poly(lactic acid) (PLA), poly (glycolic acid) (PGA) and their copolymer poly(glycolic-co-lactic acid)(PLGA). These polymers have been approved by FDA for use in surgical applications, including medical sutures. These synthetic absorbable materials have an advantage that is their degradability by simple hydrolysis of the ester backbone in aqueous environments. The final metabolin of these degradation products are carbon dioxide and water or can be excreted via the kidney.

Some useful biodegradable and/or bioabsorbable polymers include poly(lactic acid), poly(glycolic acid), polycarprolactone, polydioxane, and their random and block copolymers.

By the terminology "composite of different biodegradable and/or bioabsorbable fibers" means that a fibrous matrix contains different fibers interleaved with each other which can be in the form of a membrane or scaffold.

By the terminology "different biodegradable and/or bioabsorbable fibers" means that the article contains fibers of different biodegradable and/or bioabsorbable materials, fibers of different diameters, or fibers of different biodegradable and/or bioabsorbable materials with different diameters.

In one embodiment, the article contains different fibers having diameters in the range from a few nanometers up to 50 microns, more preferably about 50 nanometers up to about 20 microns and most preferably about 1 to about 10 microns.

By the terminology "biodegradable and/or bioabsorbable material which contains keratin" is intended at least one of the biodegradable and/or bioabsorbable fibers in the article contains keratin.

In one embodiment, the keratin particles were prepared from wool. The weight ratio of polymer and keratin is in the range of 0.1 to about 50, more preferably about 0.5 to 20.

The membranes of the present invention may be employed as substrates for cell culture. Examples of uses of the membrane of the present invention include, but are not limited to, culturing osteoblasts.

The polymer material for electrospinning is first dissolved in a solvent. The solvent can be any solvent which is capable of dissolving the polymer and providing a conducting fluid capable of being elecrospun. The solvent is preferably selected from tetrohydrofuran (THF), N—N-dimethyl acetamide (DMAc), N,N-Dimethyl formamide (DMF), chloroform, methylene chloride, dioxane, ethanol, or mixtures of these solvents.

The concentration of polymer solution is in the range of about 0.1 to about 50 wt %, more preferably about 1 to about 10 wt %. The viscosity of the conducting fluid is in the range of about 50 to about 2000 mPas, more preferably about 200 to about 700 mPas.

The range of electric field created in the electrospinning process is in a range of about 5 to about 100 kilovolts (kV), more preferably about 10 to about 50 kV. The feed rate of the conducting fluid to the spinneret will preferably be in the range of about 0.1 to about 500 ml/min, more preferably about 1 to about 100 microliters/min.

EXAMPLES

Example 1

A membrane was prepared as follows: a 1 wt % PLLA/chloroform/N,N-dimethyl formamide (DMF) solution was prepared by slowly dissolving PLLA pellets (inherent viscosity of 7.0 dl/g, PURAC, Netherlands) into a chloroform solvent at room temperature with stirring. After PLLA was completely dissolved, 10 wt % DMF was added. The solution was then loaded into the 20 ml syringe fitted with a needle, and delivered to an electrode. The solution was pumped and controlled by a syringe pump at a flow rate of 0.3 ml/min. A 10 kV positive high voltage was applied on the electrode. The distance from the tip of the electrode to the grounded collecting plate was 15 cm. A tiny electrospinning jet was formed and stabilized in 30 seconds under these conditions. The collecting plate was movable and controlled by a stepper motor. The collecting plate was continually moved at a rate of 1 mm/sec until a membrane having a relatively uniform thickness of about 100 microns was obtained. Electrospun membranes were sputtered with gold, and their morphology was observed under a scanning electron microscopy (SEM).

The morphology of electrospun fibers is influenced by various parameters such as applied voltage, solution flow rate, distance between capillary and collector, and especially the properties of polymer solutions including concentration, surface tension and the nature of the solvent. A SEM image of PLLA membrane is shown in FIG. 1.

Example 2

Figure 2:
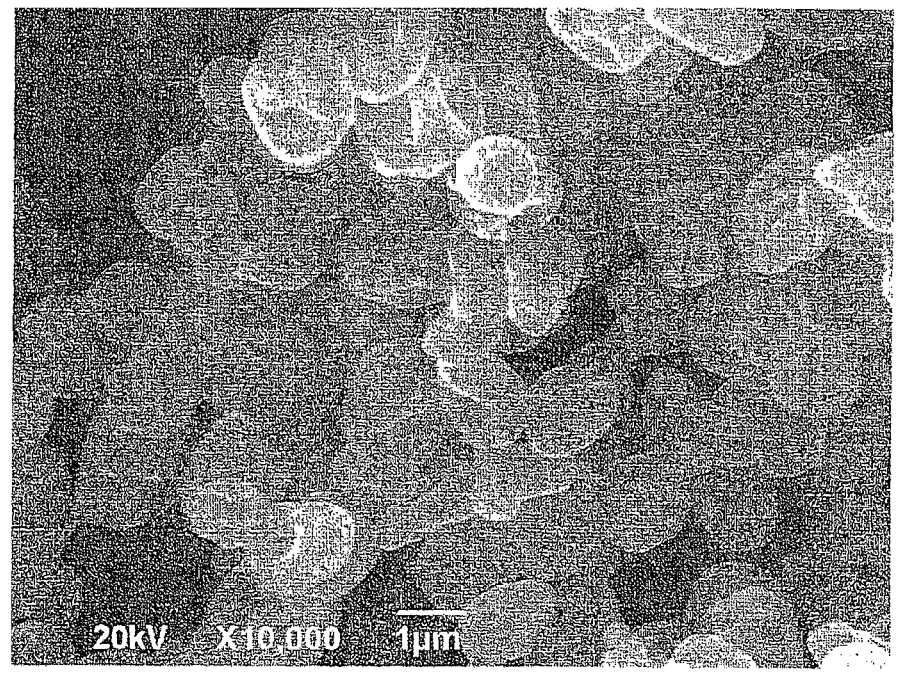
FIG. 2 is an SEM micrograph of wool keratin particles.
Figure 3:
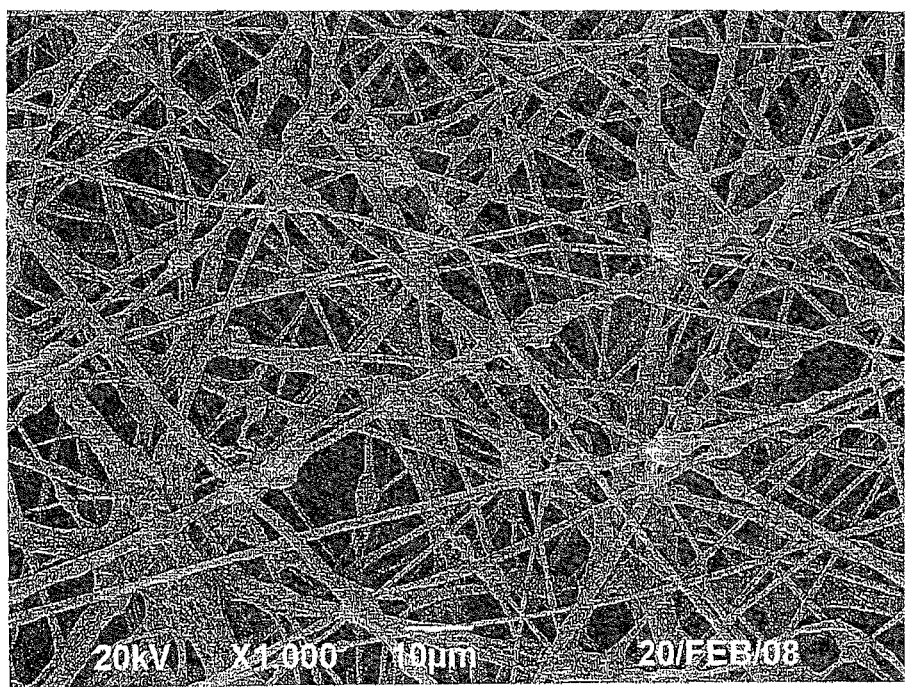
FIG. 3 is an SEM of electrospun PLLA/keratin fibrous membrane.

A biodegradable and bioabsorbable membrane with keratin according to the present invention, fabricated by an electrospinning process, was prepared as follows: 1 wt % keratin powders (FIG. 2) were dispersed in the PLLA/chloroform/DMF solution. The solution was then electrospun at 12 kV. The fibrous membrane was collected at 16 cm (FIG. 3). The membrane was examined by FTIR and SEM.

Except the parameters mentioned about, the concentration of keratin in the polymer solution also influences the fiber shape. The applied voltage, solution flow rate, distance between capillary and collector are adjusted accordingly.

Figure 4:
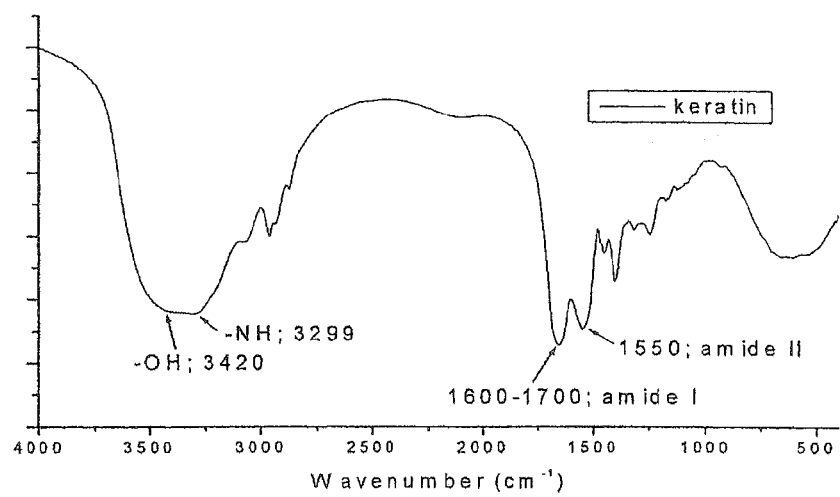
FIG. 4 is an FTIR spectra of wool keratin.
Figure 5:
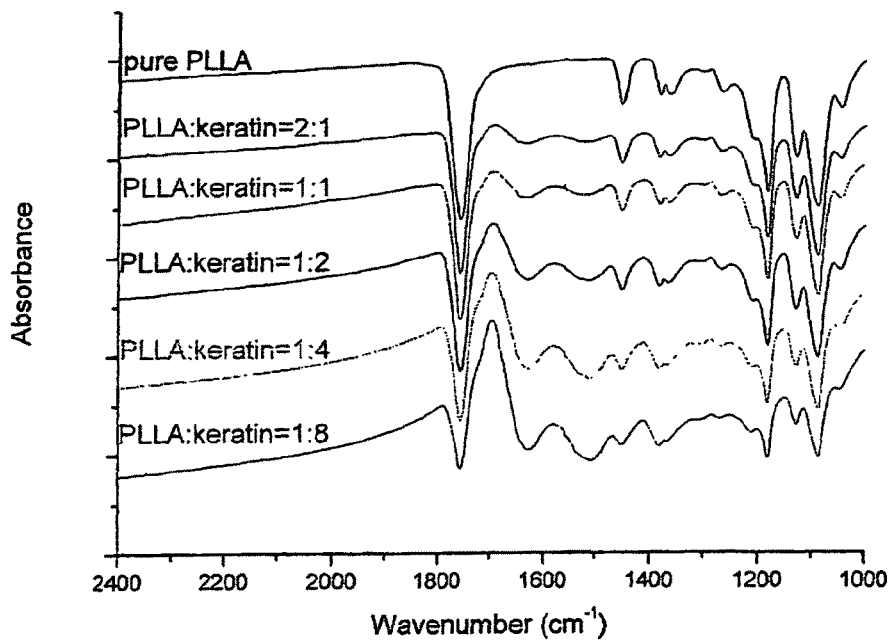
FIG. 5 is an FTIR spectra of fibrous PLLA membranes.

FIG. 4 is FTIR spectra of wool keratin. Wavenumbers from 3250 to 3300 $cm^{-1}$ are the N—H stretch which is in resonance with amide II overtone. Wavenumbers at 1600-1700 $cm^{-1}$ are mainly the C=O stretching. Wavenumber at 1550 $cm^{-1}$ is the N—H bending coupled with C—N stretching. FTIR spectra of pure PLLA have no peaks from 1700 to 1500 $cm^{-1}$. For PLLA and keratin composite membrane, two peaks appeared at 1600-1700 $cm^{-1}$ and 1550 $cm^{-1}$ which belong to keratin. With increasing of keratin in the composite, these two peaks increase correspondingly (FIG. 5).

Example 3

Figure 6:
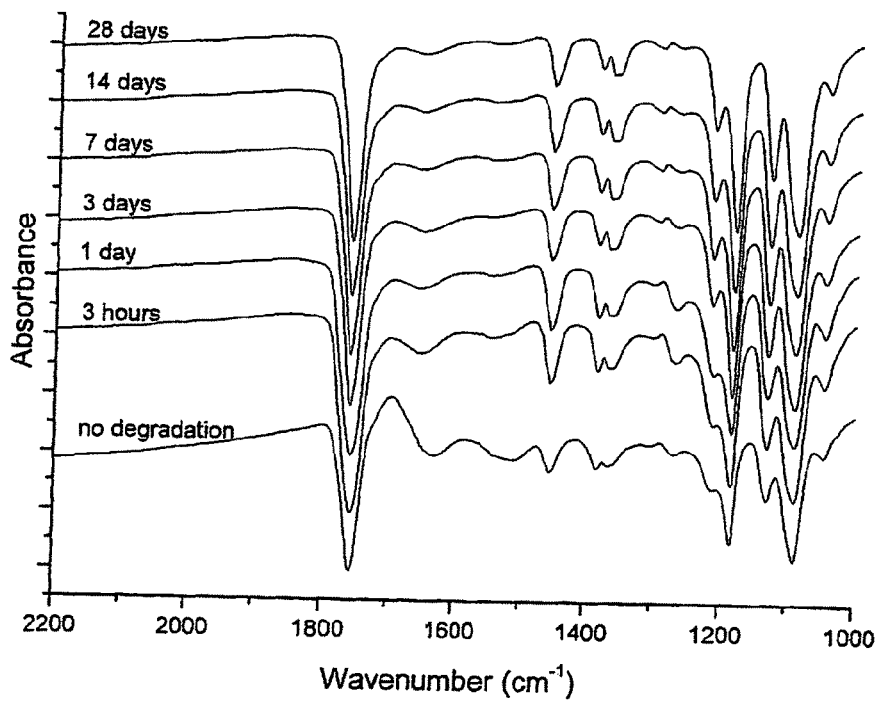
FIG. 6 is an FTIR spectra of electrospun PLLA/keratin membrane.
Figure 7:
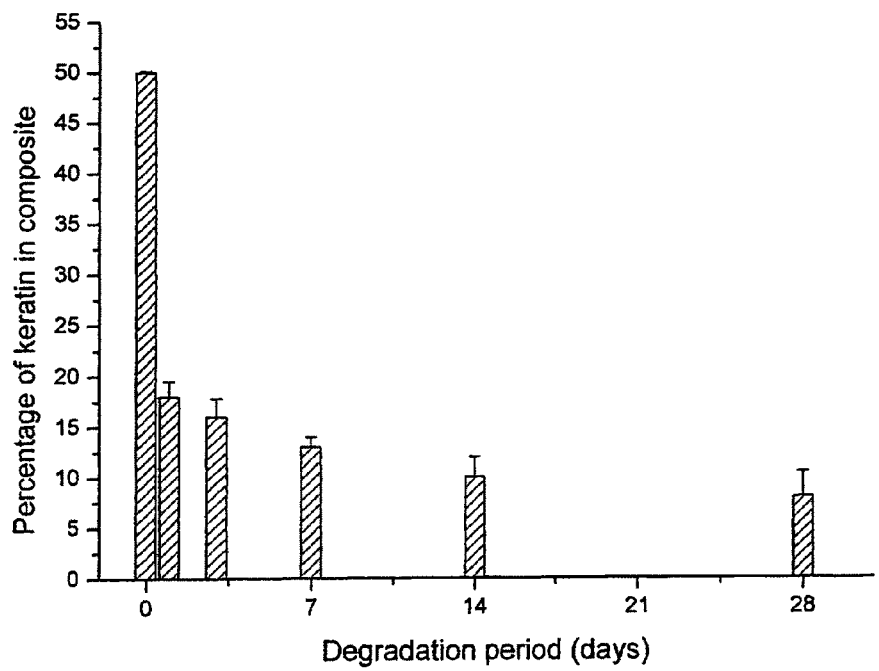
FIG. 7 shows the percentage change of keratin in PLLA/keratin.
Figure 8:
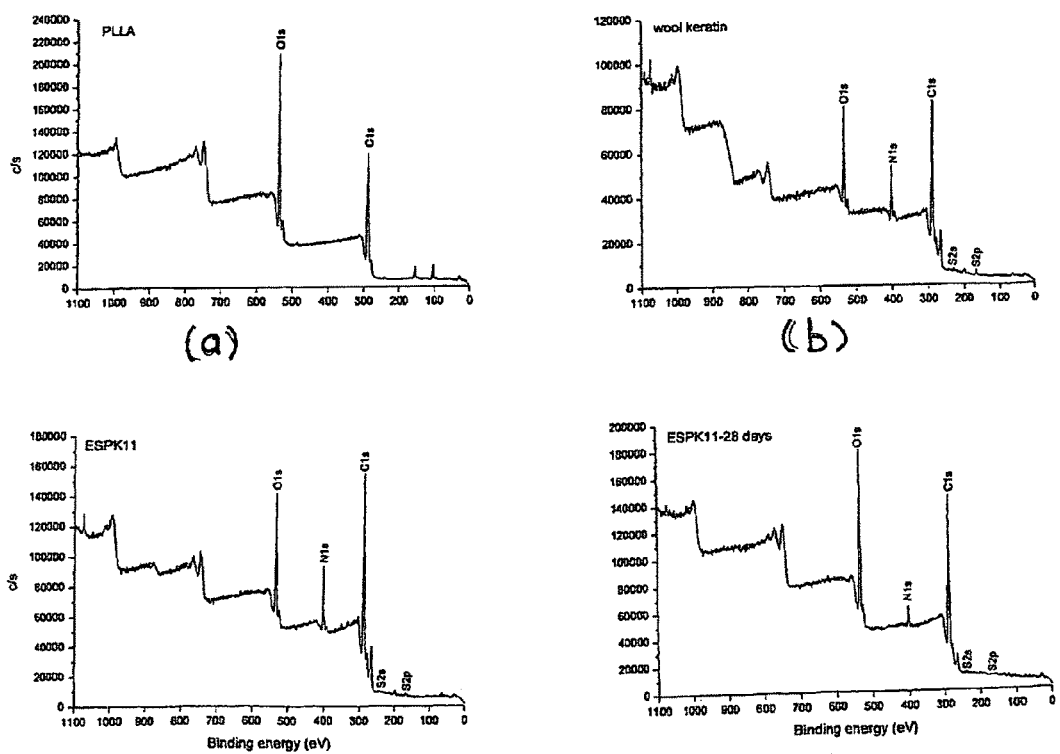
FIG. 8 shows XPS wide scan spectra.

PLLA/keratin (1:1) membranes were immersed phosphate buffer saline (PBS, pH 7.4) at 37° C. for various time periods up to 4 weeks. The degradation medium was changed daily for the first week, one at day 10 and day 14, and then weekly for the rest of the remaining period. Samples were taken out at the end of each sampling time point, i.e., at three hour, 1, 3, 7, 14, and 28 days. The samples removed from the PBS were first rinsed with distilled water and then vacuum dried for 24 h. PLLA/keratin samples before and after degradation were examine by Fourier transform infrared (FTIR) and X-ray photoelectron spectroscope (XPS) The characterizing peaks of PLLA and keratin were used to calculate their ratios after different degradation periods. Along with degradation period, the characterization peaks of keratin decreased correspondingly (FIG. 6). According to the reducing of absorbance in FTIR spectra, the change of keratin in composite was calculated (FIG. 7). In XPS wide scan spectra (FIG. 8), it was found that (1) XPS spectra of pure PLLA showed only carbon and oxygen peaks, as expected; (2) a peak with binding energy at 400 eV corresponding to nitrogen (NIs) was detected. It is well known that it is characteristics amino acid residues in the keratin; (3) peaks corresponding to N appeared on the spectra of electrospun PLLA/keratin membrane; (4) the signals of nitrogen (N1s), the characteristics elements of keratin, were present in the spectra of PLLA/keratin composite after 3 hours degradation.

Figure 9:
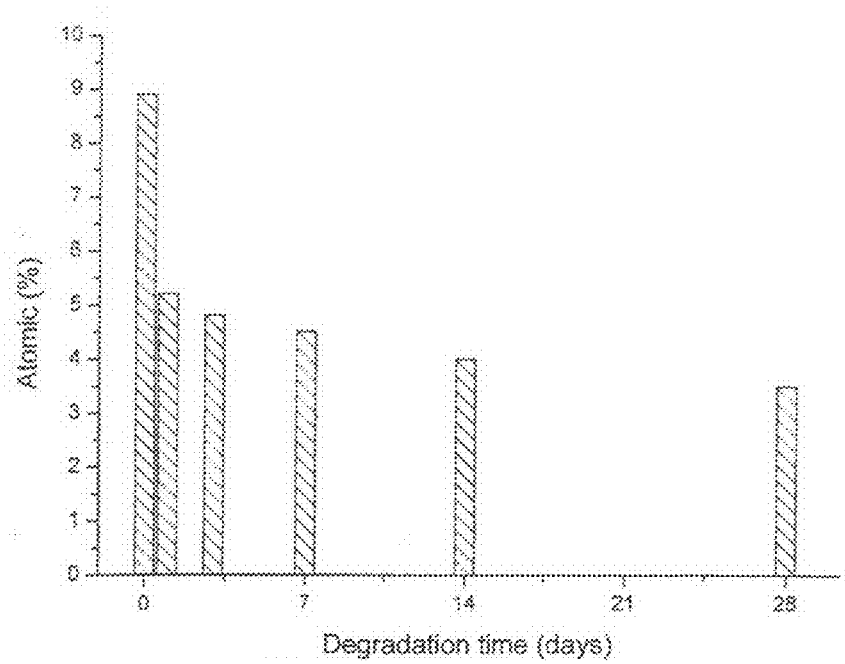
FIG. 9 shows the atomic change of the surface of PLLA/keratin membranes with degradation time.

The chemical compositions of the PLLA/keratin membranes after different degradation periods were calculated from the XPS survey scan spectra and showed in FIG. 9. The nitrogen content of PLLA/keratin (8.9%) was lower than that of pure keratin (12.6%) because of zero nitrogen content in PLLA. At the first degradation stage, the N content decreased significantly. Along with degradation time, the content of N decreased because of the lost of keratin. After 28 days degradation, nevertheless 3% atomic of N was still detected which was contribute by keratin on the PLLA fibers.

Example 4

MC3TS osteoblasts were cultured at 37° C. in a humidified atmosphere of 5% $CO_2$ in air, in flasks containing 6 ml Dulbecco's modified Eagle's medium (DMEM; Gibco), 10.0% fetal bovine serum (FBS; Gibco) and 1% penicillin/streptomycin. The medium was changed every third day. After 7-day culture, the MC3TS cells were removed from the flask, using trypsin, centrifuged, and resuspended in DMEM medium to adjust cell density to $4\times10^6$ cells/ml. 25 µl (about $1\times10^5$ cells) of the cell suspensions were seeded evenly into the PLLA/wool keratin (1:4 in weight) membranes with a micropipette. The seeded membranes were maintained in incubator for 2 h and culture medium was added to the wells. The medium was changed every 2 days. After incubation, any non-adherent cells on the samples were removed by aspirating the medium and washing with PBS solution.

After 7 days of culture, cellular constructs were harvested, rinsed twice with PBS to remove non-adherent cells and subsequently fixed with 2.5% glutaraldehyde at 4° C. for 4 h. After that, the samples were dehydrated through a series of graded ethanol solutions and air-dried overnight. Dry cellular constructs were sputtered with gold and observed by SEM.

Figure 10:
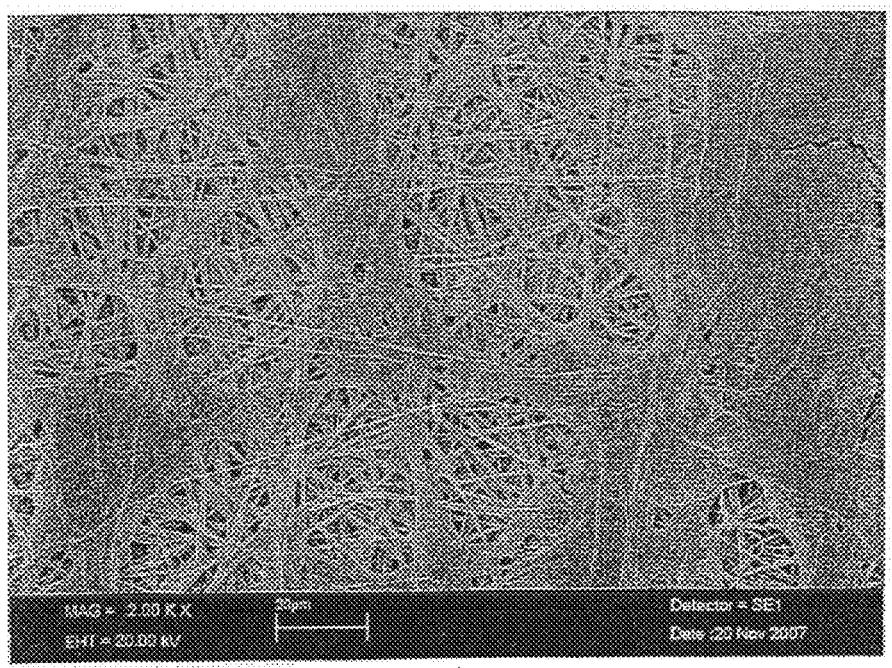
FIG. 10 is an SEM micrograph of osteoblasts on PLLA/keratin fibrous membrane.
Figure 11:
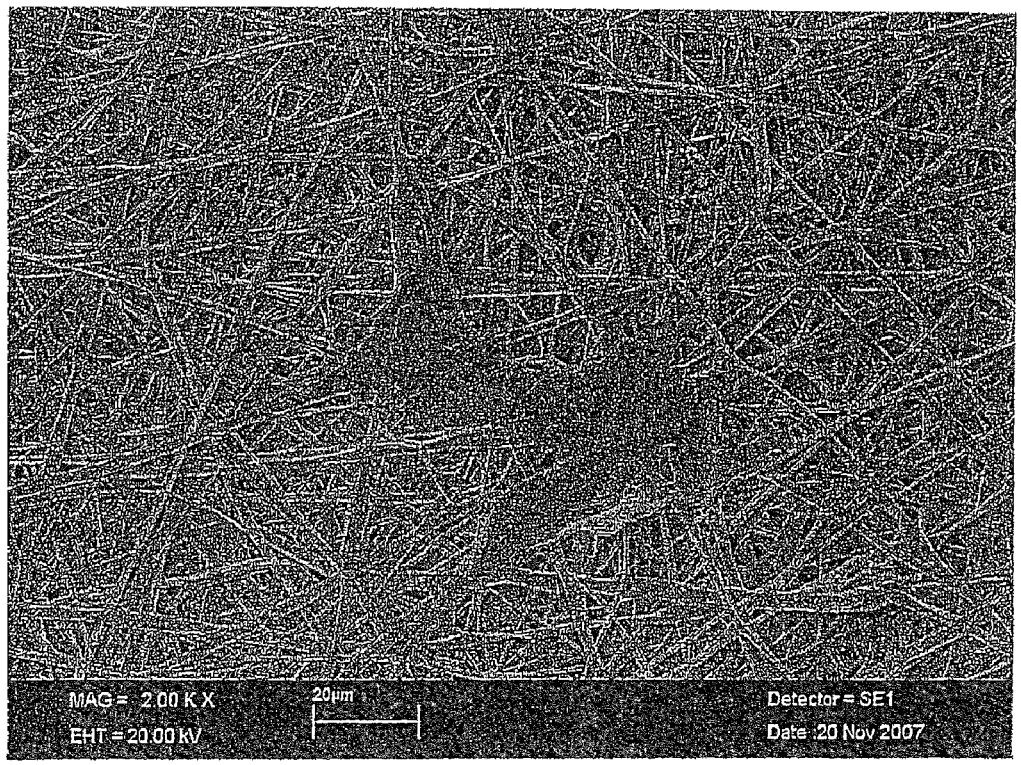
FIG. 11 is an SEM micrograph of osteoblasts on pure PLLA fibrous membrane.

SEM results showed that more cells were observed on PLLA/wool keratin membranes (FIG. 10) than that on PLLA membrane control (FIG. 11).

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:
a) the word "comprising" does not exclude the presence of other elements or acts than those listed in the given claim;
b) the word "a" or "an" preceding an element does not exclude the presence of a plurality of such elements;
c) any reference signs in the claims do not limit their scope;
d) any of the disclosed devices or portions thereof may be combined together or separated into further portions unless specifically stated otherwise; and
e) no specific sequence of acts or steps is intended to be required unless specifically indicated.

The invention claimed is:

1. A method of making a biomaterial and keratin nonwoven fibrous article comprising the steps:
   (a) dissolving keratin and a macromolecule material for electrospinning in a solvent to result in a solution;
   (b) delivering said solution to an electrode;
   (c) applying a voltage to said electrode;
   (d) moving a collecting plate until a membrane is obtained; and
   (e) sputtering said membrane with a metal; wherein said solvent is selected from the group consisting of tetrahydrofuran, N-N-dimethyl acetamide, N,N-dimethyl formamide, chloroform, methylene chloride, dioxane, ethanol, and a mixture of the previous solvents.

2. The method of making a biomaterial and keratin nonwoven fibrous article of claim 1, wherein said macromolecule is selected from the group consisting of glycolide, lactide, dioxanone, caprolactone, trimethylene carbonate, ethylene glycol, lysine, a homopolymer, random co-polymer, block co-polymer, and hetero-polymer.

3. The method of making a biomaterial and keratin nonwoven fibrous article of claim 2, wherein said macromolecule further comprises a polyester such as poly(lactic acid), poly (glycolic acid), or copolymer poly(glycolic-co-lactic acid).

4. The method of making a biomaterial and keratin nonwoven article of claim 1, wherein said solution has a concentration of from about 0.1 to about 50 wt %.

5. The method of making a biomaterial and keratin nonwoven article of claim 4, wherein said solution has a concentration of from 1 to about 10 wt %.

6. The method of making a biomaterial and keratin nonwoven article of claim 1, wherein said voltage is from about 5 to about 100 kV.

7. The method of making a biomaterial and keratin nonwoven article of claim 6, wherein said voltage is from about 10 to about 50 kV.

8. The method of making a biomaterial and keratin nonwoven article of claim 1, wherein delivering said solution to an electrode comprises pumping the solution at a flow rate of between about 0.1 to about 500 mL/min.

* * * * *